(12) United States Patent
Bowsher

(10) Patent No.: US 11,058,839 B2
(45) Date of Patent: Jul. 13, 2021

(54) SEALING CUSHION WITH INNER MEMBRANE

(71) Applicant: INTERSURGICAL AG, Vaduz (LI)

(72) Inventor: Richard Francis Bowsher, Wokingham (GB)

(73) Assignee: INTERSURGICAL AG, Vaduz (LI)

( * ) Notice: Subject to any disclaimer, the term of this patent is extended or adjusted under 35 U.S.C. 154(b) by 489 days.

(21) Appl. No.: 15/107,785

(22) PCT Filed: Dec. 23, 2014

(86) PCT No.: PCT/EP2014/079274
§ 371 (c)(1),
(2) Date: Jun. 23, 2016

(87) PCT Pub. No.: WO2015/097265
PCT Pub. Date: Jul. 2, 2015

(65) Prior Publication Data
US 2016/0339196 A1    Nov. 24, 2016

(30) Foreign Application Priority Data
Dec. 24, 2013  (GB) ..................... 1323010

(51) Int. Cl.
*A61M 16/06*  (2006.01)
*A61M 16/00*  (2006.01)

(52) U.S. Cl.
CPC .... *A61M 16/0622* (2014.02); *A61M 16/0057* (2013.01); *A61M 16/06* (2013.01);
(Continued)

(58) Field of Classification Search
CPC .......... A61M 16/0622; A61M 16/0616; A61M 16/0644; A61M 16/0057; A61M 16/06;
(Continued)

(56) References Cited

U.S. PATENT DOCUMENTS 4,907,584 A * 3/1990 McGinnis ............. A61M 16/06
128/206.24
4,951,664 A    8/1990 Niemeyer
(Continued)

FOREIGN PATENT DOCUMENTS

EP    0196204 A2    10/1986
EP    0264772 A1    4/1988
(Continued)

OTHER PUBLICATIONS

Search Report for corresponding Great Britain Application No. 1323010.7 (dated Oct. 8, 2014).
(Continued)

*Primary Examiner* — Jan Christopher L Merene
*Assistant Examiner* — Brian T Khong
(74) *Attorney, Agent, or Firm* — Troutman Pepper Hamilton Sanders LLP (Rochester)

(57) ABSTRACT

A sealing cushion for a respiratory mask assembly has a patient interface portion having a resiliently deformable membrane for engagement with a patient's face, and an aperture formed therein for receiving a nasal and/or mouth region of the patient's face. An inner surface of the deformable membrane comprises a plurality of projections arranged in separate groups of projections positioned in a plurality of localized regions of the deformable membrane. The projections in each of the separate groups of projections are arranged such that each projection in the group of projections engages with an adjacent projection in the group of projections when the deformable membrane is deformed during engagement of the deformable membrane with the patient's face, in use, thereby providing the deformable membrane with an increased resistance to further deformation.

23 Claims, 11 Drawing Sheets

(52) U.S. Cl.
CPC .... *A61M 16/0616* (2014.02); *A61M 16/0644* (2014.02); *A61M 16/0683* (2013.01); *A61M 2209/08* (2013.01)

(58) Field of Classification Search
CPC .......... A61M 16/0683; A61M 16/0633; A61M 2209/08; A62B 18/02; A62B 18/00; A62B 18/025; A61G 7/05707; A61G 7/057; A47C 27/142; Y10S 5/944; A41D 13/1176; A42B 3/065; A42B 3/32
See application file for complete search history.

(56) References Cited

U.S. PATENT DOCUMENTS

| | | | |
|---|---|---|---|
| 4,967,433 A * | 11/1990 | Neal | A47C 27/146 5/655.9 |
| 4,971,051 A | 11/1990 | Toffolon | |
| 5,153,956 A * | 10/1992 | Nold | A61G 7/05707 428/218 |
| 5,209,226 A | 5/1993 | Goodley | |
| 5,469,842 A | 11/1995 | Flynn | |
| 5,494,725 A * | 2/1996 | Fejes | A47C 27/00 297/452.39 |
| 5,570,689 A | 11/1996 | Starr et al. | |
| 6,467,483 B1 * | 10/2002 | Kopacko | A61M 16/06 128/205.25 |
| 7,827,990 B1 | 11/2010 | Melidis et al. | |
| 8,051,855 B2 * | 11/2011 | Ho | A61M 16/06 128/206.21 |
| 9,132,255 B2 * | 9/2015 | Skipper | A61M 16/06 |
| 9,242,062 B2 | 1/2016 | Melidis | |
| 9,907,924 B2 * | 3/2018 | Eury, Jr. | A61M 16/0611 |
| 2003/0014496 A1 | 1/2003 | Spencer et al. | |
| 2003/0019495 A1 | 1/2003 | Palkon et al. | |
| 2003/0019496 A1 | 1/2003 | Kopacko et al. | |
| 2004/0118406 A1 | 6/2004 | Lithgow et al. | |
| 2006/0225740 A1 | 10/2006 | Eaton et al. | |
| 2007/0267017 A1 | 11/2007 | McAuley et al. | |
| 2008/0006277 A1 * | 1/2008 | Worboys | A61M 16/06 128/207.13 |
| 2008/0178886 A1 | 7/2008 | Lieberman et al. | |
| 2008/0256686 A1 * | 10/2008 | Ferrara | B60R 19/20 2/413 |
| 2008/0257354 A1 * | 10/2008 | Davidson | A61M 16/06 128/206.24 |
| 2010/0043798 A1 | 2/2010 | Sullivan et al. | |
| 2011/0146684 A1 | 6/2011 | Wells et al. | |
| 2013/0014760 A1 * | 1/2013 | Matula, Jr. | A61M 16/06 128/205.25 |
| 2014/0007322 A1 * | 1/2014 | Marz | A42B 3/065 2/411 |
| 2014/0144448 A1 | 5/2014 | Eifler | |
| 2015/0157823 A1 * | 6/2015 | Eury, Jr. | A61M 16/0611 128/205.25 |
| 2016/0367778 A1 | 12/2016 | Eves et al. | |

FOREIGN PATENT DOCUMENTS

| | | |
|---|---|---|
| EP | 0686408 A2 | 12/1995 |
| EP | 0838237 A2 | 4/1999 |
| EP | 1258266 A1 | 11/2002 |
| EP | 1982740 A2 | 10/2008 |
| EP | 2266652 A1 | 12/2010 |
| EP | 1582231 B1 | 7/2012 |
| FR | 2076334 | 10/1971 |
| GB | 837250 | 6/1960 |
| GB | 2266669 A | 11/1993 |
| GB | 2336547 A | 10/1999 |
| WO | 2001/32250 A1 | 5/2001 |
| WO | 2001/62326 A1 | 8/2001 |
| WO | 2005/118040 A1 | 12/2005 |
| WO | 2006/074513 A1 | 7/2006 |
| WO | 2006/074514 A1 | 7/2006 |
| WO | 2006074515 | 7/2006 |
| WO | 2009/022249 A2 | 2/2009 |
| WO | 2010/016774 A1 | 2/2010 |
| WO | 2010/135785 A1 | 12/2010 |
| WO | 2010/148453 A1 | 12/2010 |
| WO | 2013/006065 A1 | 1/2013 |
| WO | 2013/026091 A1 | 2/2013 |
| WO | 2013/108145 A1 | 7/2013 |
| WO | 2013/108160 A1 | 7/2013 |
| WO | 2013/186650 A1 | 12/2013 |
| WO | 2014/141029 A1 | 9/2014 |
| WO | 2015/070289 A1 | 5/2015 |

OTHER PUBLICATIONS

International Search Report and Written Opinion for corresponding PCT Application No. PCT/EP2014/079274 (dated Jul. 15, 2015).
Search Report for corresponding Great Britain Application No. GB1323010.7 (dated Apr. 22, 2015).
Search Report for corresponding Great Britain Application No. GB1323010.7 (dated Oct. 8, 2014).

* cited by examiner

SEALING CUSHION WITH INNER MEMBRANE

This application is a U.S. national stage application under 35 U.S.C. § 371 of PCT Application No. PCT/EP2014/079274, filed Dec. 23, 2014, which claims the priority benefit of Great Britain Patent Application Serial No. 1323010.7 filed Dec. 24, 2013.

The present invention relates to respiratory masks, such as respiratory mask assemblies for use in non-invasive ventilation, and sealing cushions therefor.

Non-invasive ventilation is a process by which a flow of respiratory gas is delivered to the airway of a patient through a non-invasive interface device, which is generally a respiratory mask, and hence without using an invasive device that enters a patient's airway, such as an endotracheal tube. Non-invasive ventilation is typically used to manage both chronic and acute respiratory failure, and also other medical disorders, such as sleep apnoea.

Leakage from a respiratory mask during use is undesirable because it reduces alveolar ventilation and synchrony between the patient and the ventilator, and hence respiratory masks for use in non-invasive ventilation are generally adapted to form an effective seal against the patient's face. For this reason, resiliently deformable sealing cushions are typically provided as a patient interface portion of a respiratory mask.

Whilst such sealing cushions are able to resiliently deform to generally match the contours of a patient's face, there nevertheless remain gaps between the sealing cushion and the patient's face which allow leakage of the respiratory gas. In order to eliminate such leakage it is necessary to apply further force, usually through the use of an elasticated band or strap, to further engage the sealing cushion with a patient's face, thus eliminating any gaps in the seal.

This can, however, cause discomfort to the patient, e.g. pressure sores. Furthermore, over deformation of the sealing cushion can cause unwanted stress in the material of the device, which may eventually lead to degradation and failure of the cushion, and may also result in improper location of the sealing cushion, allowing the sealing cushion to move from its desired location during use.

There has now been devised an improved respiratory mask assembly, an improved sealing cushion therefor, which overcome or substantially mitigate the aforementioned and/or other disadvantages associated with the prior art.

According to a first aspect of the invention there is provided a sealing cushion for a respiratory mask assembly, the sealing cushion comprising a patient interface portion having a resiliently deformable membrane for engagement with a patient's face, and an aperture formed therein for receiving a nasal and/or mouth region of a patient's face, wherein an inner surface of the membrane comprises a plurality of projections, the projections being arranged such that each projection is engageable with an adjacent projection on deformation of the membrane during engagement of the membrane with the patient's face, in use, thereby providing the membrane with an increased resistance to deformation in a deformed configuration.

The sealing cushion according to the invention is advantageously principally as it enables an arrangement having two stages of operation: a first stage in which the sealing cushion provides a lower resistance to deformation and hence a lower resilience (e.g. when projections do not engage adjacent projections), allowing the sealing cushion to be properly located against the face of the patient; and a second stage in which the sealing cushion provides a higher resistance to deformation and hence a higher resilience (e.g. when projections are engaged with adjacent projections), allowing the sealing cushion to sealingly engage with the face of the patient, whilst resisting over-deformation. The sealing cushion according to the invention also enables an arrangement in which the sealing cushion has a sufficiently high resistance to deformation towards the patient, when fitted to a patient, but provides a lower resistance to deformation away from a patient's face, e.g. upon application of pressurised gases to the respiratory mask.

The projections may be upstanding from the inner surface of the membrane. The height of the projections may be at least double, and more preferably at least three times, the thickness of the membrane. The height of the projections may be at least five times, or at least ten times, the thickness of the membrane. The width and/or length of the projections may be at least double, and more preferably at least three times, the thickness of the membrane. The width of the projections may be at least five times, or at least ten times, the thickness of the membrane.

Groups of projections (support formations) may be arranged in a plurality of localised regions of the membrane. Groups of projections may be arranged around the circumferential extent of membrane. There may be a substantially regular separation between adjacent groups of projections. Projections in a group of projections may be disposed in a regular array, or in an irregular arrangement.

Two or more groups of projections may be adapted to provide different levels of resilience and/or resistance to deformation, pre- and/or post- engagement. Two or more groups of projections may comprise different numbers of projections. Two or more groups of projections and/or two or more individual projections may be shaped, sized and/or arranged to provide different levels of resilience and/or resistance to deformation. Groups of projections may differ in overall size in different localised regions of the membrane. For example, groups of projections located in a nasal bridge region of the membrane may be larger than groups of projections located in lower corners of the membrane. The projections in a group of projections may extend substantially transversely across the membrane, e.g. aligned along a substantially transverse axis. The projections may extend transversely across substantially the entirety of the membrane. The projections may extend transversely only partially across the membrane.

Groups of projections may be located either side of a nasal bridge region and/or in lower corners of the membrane adjacent nostrils in a nasal mask or adjacent sides of the mouth in a full face mask.

At least two groups of projections may have substantially the same global form. One or more pairs of groups of projections may have substantially the same global form. One or more opposing pairs of groups of projections, across a substantially vertical central axis of the sealing cushion, may have substantially the same global form. Thus, the same force may be applied on each side of the sealing cushion.

The global form of one or more of the groups of projections may be tapered. One or more of the groups of projections and/or individual projections may be tapered along its length. One or more of the groups of projections and/or individual projections may have a lower width and/or height in a region of the membrane that is adjacent to the aperture.

One or more of the projections may be tapered in a transverse direction. For example, the projection may reduce in width and/or height towards an inner edge of membrane which defines the aperture. This may thereby provide a region of greater flexibility and/or less resilience in the region of the membrane adjacent to the aperture.

One or more of the projections may be tapered in a circumferential direction. For example, the projections may reduce in height at outer edges of a group of projections. Thus, the projections may provide a graduated transition between regions of greater, and regions of lesser, resilience and/or resistance to deformation.

The plurality of projections may be integrally formed with the membrane. The plurality of projections may be formed as part of the same moulding process that forms the membrane. The plurality of projections may be formed of the same material as the membrane.

The projections may be aligned substantially transversely across the membrane. The projections may extend transversely across substantially the entirety of the membrane. The projections may extend transversely only partially across the membrane.

A group of projections may comprise two projections only. Alternatively, a group of projections may comprise a series of three or more projections, e.g. substantially aligned along a transverse axis, which may be adapted to engage an adjacent projection substantially simultaneously, or there may be staged engagement as deformation of the membrane increases. For example, at least two projections in a first region of the membrane, e.g. in a region adjacent to the aperture for receiving a nasal and/or mouth region of a patient's face, may be adapted to engage one another before engagement of at least two projections in a second region of the membrane, e.g. in a region having a greater separation from the aperture than the first region, during engagement of the membrane with the patient's face, in use.

Each of the projections may comprise an abutment surface, which is brought into abutment with a corresponding abutment surface of an adjacent projection, in use, in a deformed configuration of the membrane. One or more of the abutment surfaces may be adapted to resist transverse movement/slippage when it is engaged with an adjacent abutment surface.

The abutment surface may be shaped to resist transverse movement/slippage when engaged with an adjacent abutment surface. Adjacent abutment surfaces may have the same or correspondingly shaped surfaces. For example, each abutment surface may be substantially planar, or each abutment surface may have formations that substantially mate with corresponding formations of an adjacent abutment surface. Thus, there may be less risk of slippage, and hence more predictable resistance to deformation of the membrane. The abutment surface may comprise a rough surface. The abutment surface may thereby increase frictional contact with an adjacent abutment surface.

Adjacent abutment surfaces of the projections may define a channel or a groove. The channel or groove may have a substantially constant width. Thus, the channel or groove may allow for substantially simultaneous engagement between different portions of adjacent projections, thereby providing a more rapid transition between the membrane's different resistances to deformation and/or resilience.

At least one, or each, projection may be at least partially separated from an adjacent projection in a rest configuration of the sealing cushion. At least one, or each, projection may be separated entirely from an adjacent projection, i.e. from the inner surface of the membrane. This may provide greater flexibility of the membrane before the engagement of adjacent projections. Alternatively, one or more, or each, of the projections may be separated from an adjacent projection by a substantially "V-shaped" channel or groove. Thus, there may be a greater resistance to deformation and/or greater resilience prior to the engagement of adjacent projections, in these embodiments. Alternatively, it may be possible to achieve differing resistances to deformation utilising projections that are in abutment, e.g. with a low contact pressure, in a rest configuration. For example, such projections may be formed by cutting through a projection to form two abutting projections during manufacture.

The membrane may comprise an outer contact surface for contacting the patient's face. The outer contact surface may be shaped in the rest configuration to substantially match contours of a patient's face. The membrane may present a convex contact surface to patient's face. The membrane may be curved in cross-section in the region of the contact surface. The curvature of the membrane may increase on deformation caused by engagement with the patient's face. This may allow projections to engage adjacent projections upon sufficient deformation of the membrane. The membrane may be curved in cross-section between a side wall adjacent to a connection to a mask shell and the region of the contact surface.

The membrane may be formed of any resiliently deformable material suitable for use in the sealing cushion of a mask assembly. The membrane may be formed of a thermoplastic elastomer (TPE) or a thermoset elastomer (TSE), such as silicone.

The membrane may have a substantially uniform thickness in regions which do not comprise projections. Alternatively, the membrane may comprise regions of a different thickness than the remainder of the membrane, thereby providing regions of lower and/or higher flexibility and/or resilience. The membrane may comprise a single membrane. For example, the membrane may have no underlying support member and/or cushion, such that the only resistance to deformation is provided by the membrane and associated projections.

Where the membrane is curved in cross-section in the region of the contact surface, and where the curvature increases on deformation caused by engagement with patient's face, the engagement between adjacent projections may be caused by the increase in curvature of the membrane.

Each projection may not necessarily be in engagement with an adjacent projection when the mask is fitted to a patient, and the projections that are in engagement may change as the patient and mask moves, in use. In particular, depending on the patient's particular fit of the mask and/or the pressure of the respiratory gases for the treatment supplied, the projections may not all come into abutment. The projections may be disengaged, e.g. separated, in use, e.g. upon application of pressurised gases to the respiratory mask.

The engagement between adjacent projections may increase the resilience of the membrane to deformation. A series of three or more adjacent projections may be brought into engagement substantially simultaneously, or there may be staged engagement as deformation of the membrane increases. For example, at least two projections in a first region of the membrane, e.g. in a region adjacent to the aperture for receiving a nasal and/or mouth region of a patient's face, may be adapted to engage one another before engagement of at least two projections in a second region of the membrane, e.g. in a region having a greater separation from the aperture than the first region, during engagement of the membrane with the patient's face, in use.

The aperture may be disposed substantially centrally within the membrane. The aperture may conform substantially to the shape of a nasal and/or mouth region of a patient.

The aperture may be substantially triangular in shape. The aperture may comprise a nasal bridge portion with a reduced width relative to an adjacent lower nasal portion. The corners of the aperture may be rounded or curved.

The membrane in the region of the aperture may be adapted so as to increase the comfort of a patient. The membrane in the region of the aperture may be shaped so as to increase the comfort of a patient. The membrane in the region of the aperture may curve slightly inwardly towards an internal cavity of the mask cushion.

The sealing cushion may comprise a mask interface portion for connection to a mask body. The mask interface portion may be, and is most preferably, disposed on an opposing end of the sealing cushion to the patient interface portion. The mask body will typically define a cavity for receiving a nasal and/or mouth region of a patient's face, and will typically include a gas inlet/outlet for respiratory gases.

The sealing cushion may be adapted to fasten, in a peripheral region, to a mask body, which may be more rigid than the sealing cushion and have the form of a mask shell. In particular, the mask interface portion may comprise a recess for receiving a corresponding projection of a mask shell, e.g. with a close fit and/or a snap fit.

The sealing cushion may be adapted to engage with a fastener portion of a mask shell. For example, the sealing cushion may be adapted to receive at least one clip or the like. In particular, the mask interface portion may comprise a recess adapted to receive enlarged portions of a corresponding projection of a mask shell.

Thus, the sealing cushion may be connected to a mask shell which comprises a gas inlet and/or outlet. The sealing cushion may form part of a nasal mask assembly for accommodating the nose only. The sealing cushion may form part of a "full face" mask assembly for accommodating the nose and mouth.

The sealing cushion may be a unitary component. The sealing cushion may be formed via a single moulding process, for example by injection moulding or the like.

According to a second aspect of the present invention there is provided a respiratory mask assembly comprising a sealing cushion according to the first aspect of the present invention.

The respiratory mask assembly may comprise a mask shell, which may be more rigid than the sealing cushion. The mask shell may be adapted so as to define an internal cavity. The mask shell may be generally dome-shaped so as to define an internal cavity. The mask shell may have a substantially concave interior surface. The mask shell may have a substantially convex exterior surface. The internal cavity may be, and is most preferably, in direct fluid communication with an internal cavity of the sealing cushion.

The mask shell may be adapted to permanently engage the sealing cushion. Alternatively, and most preferably, the mask shell may be adapted to releasably engage the sealing cushion.

A rear surface of the mask shell may comprise at least one projection, which may extend around a peripheral region of the mask shell. The at least one projection may be shaped and/or dimensioned so as to be received by a corresponding recess of the mask shell interface portion of the sealing cushion.

The mask shell may comprise at least one fastener portion. The at least one fastener portion may be disposed in one or more localised regions of the rear surface of the mask shell. A fastener portion may be disposed along each edge of the mask shell, but may be omitted from one or more corners of the mask shell to facilitate disengagement. The at least one fastener portion may form part of a projection received by a corresponding recess of the mask shell interface portion of the sealing cushion, but may have dimensions larger than those of the remainder of the projection.

The at least one fastener portion may be adapted to engage, and most preferably releasably engage, a corresponding clip receiving portion of the mask interface portion. The at least one fastener portion may be shaped to engage, and most preferably releasably engage, a corresponding clip receiving portion of the mask interface portion. The at least one fastener portion may be a clip or the like.

The mask shell may comprise an aperture adapted to engage a fluid connector, or may have a fluid connector formed integrally therewith. The fluid connector may be an elbow connector. The mask shell may comprise a connecting formation, which is adapted to connect the mask shell to a fluid connector, such that the fluid connector is in fluid communication with the aperture.

The connecting formation may rotatably mount the fluid connector to the mask shell. The connecting formation of the mask shell, and the fluid connector, may comprise corresponding formations that engage one another at one or more predetermined rotational positions of the fluid connector, relative to the mask shell, such that the fluid connector is retained in the predetermined rotational position during use, until manually moved by a user, for example. The one or more predetermined rotational positions of the fluid connector may include a position in which the distal end of the fluid connector is directed in the direction of a longitudinal axis of the patient's face, e.g. upwardly with respect to the patient's face, to maintain a connected respiratory tube over the top of the patient's head, if they find this a more comfortable position to sleep.

The connecting formation may be disposed on an exterior surface of the mask shell. The connecting formation may be upstanding from the exterior surface of the mask shell. The connecting formation may be integrally formed with the mask shell. The connecting formation may take the form of a ridge, or projection, or the like. The connecting formation may be located in a region adjacent to the aperture. The connecting formation may extend around substantially the entirety of the aperture. The connecting formation may have a substantially constant cross-section.

The connecting formation may further comprise at least one locking projection. The at least one locking projection may be adapted so as to permanently engage a corresponding receiving portion of a fluid connector. The at least one locking projection may be locatable within a corresponding receiving portion of the fluid connector.

The respiratory mask assembly may comprise a fluid connector for connecting the mask assembly to the remainder of a respiratory circuit. The connector may comprise first and second limbs in fluid communication. The first and second limbs may be disposed substantially perpendicularly to each other, such that the connector has an "L-shape". The connector may be a so-called elbow connector.

The interface between the first and second limbs may be tapered, thereby allowing a reduced projection of the connector from the mask shell. In particular, the conduit defined by the first, distal limb may gradually reduce in dimension, e.g. along an axis perpendicular to the patient's face, such that the first, distal limb is depressed towards the patient's face, relative to a conventional elbow conduit of substantially constant cross-sectional dimensions.

The connector may be adapted to fixedly engage a mask shell at a proximal end. The connector may comprise a peripheral rim at a proximal end for releasably receiving a corresponding fastening and/or locking formation of a mask shell.

The respiratory mask assembly may comprise at least one, and most preferably a plurality of, vent formations. The at least one vent formation may be formed in the connector, e.g. in the wall of the connector. The at least one vent formation may be adapted to direct exhaled respiratory gases out of the respiratory mask assembly, e.g. in a direction substantially away from the patient's face.

The at least one vent formation may comprise an aperture, and may comprise a groove or channel for directing gas from the interior of the mask towards and through the aperture. The aperture may be exposed on an exterior surface of the connector, e.g. at the interface between the first and second limbs of the connector. The groove or channel may be disposed on an interior surface of the connector, e.g. at the interface between the first and second limbs of the connector. The groove or channel may be tapered along its length. Each aperture may be in fluid communication with a corresponding groove or channel. Thus, each groove or channel may direct air through an aperture, and out of the connector formation.

The connector may comprise at least one formation at its distal end for releasably connecting to a fluid connector of another component of a respiratory circuit. The connector may be actuable between first and second configurations. The first configuration may retain a fluid connector of respiratory tubing or any other such appropriate respiratory circuit component. The second configuration may release a fluid connector of respiratory tubing or any other such appropriate respiratory circuit component. The at least one connecting formation may comprise a plurality of slots. Each of the plurality of slots may be shaped and/or dimensioned so as to receive a corresponding portion of a respiratory tube, or any other such appropriate respiratory circuit component.

The at least one connecting formation may be actuated from a first configuration to a second configuration via the application of pressure. Such a configuration allows a respiratory tube to be quickly and easily connected and/or disconnected from the mask assembly via depression of the at least one connecting formation. Such a configuration is thereby simpler and less time consuming than configurations known from the prior art.

The mask shell may comprise at least one fastener for connecting to headgear for the respiratory mask assembly. The at least one fastener may be adapted to permanently retain a headgear strap or the like. The at least one fastener is most preferably adapted to releasably retain a headgear strap or the like. The at least one fastener may be shaped so as to releasably retain a headgear strap or the like. The mask shell most preferably comprises a plurality of fasteners, for example, one on each side of the mask shell.

The fastener may extend laterally outwardly from the mask shell. The fastener may extend laterally outwardly from a lower corner of the mask shell. Most preferably, a fastener extends laterally outwardly from each of the lower corners of the mask shell. The fastener may be integrally formed with the mask shell. The fastener may be adapted to receive a corresponding portion of a headgear strap or the like. The fastener may be shaped so as to receive a corresponding portion of a headgear strap or the like. The fastener may define one or more apertures, and hence have the form of a buckle, or may have the form of a hook. Where the fastener is a hook, the fastener may be substantially "C shaped" in form.

The mask may comprise first and second fasteners, each adapted to releasably retain a headgear strap or the like. In an alternative embodiment, a first fastener may be adapted so as to permanently retain a headgear strap or the like, and a second fastener may be adapted so as to releasably retain a headgear strap or the like.

The respiratory mask assembly may include a respiratory mask and headgear for retaining the respiratory mask on a patient's face, in use, wherein the headgear includes one or more flexible straps and at least one fastener adapted to releasably attach to a corresponding fastener of the respiratory mask. In presently preferred embodiments, the corresponding fasteners comprise a first fastener having a neck portion and an enlarged head portion, and a second fastener having one or more support members defining an opening for accommodating the neck portion of the first fastener, such that the enlarged head portion of the first fastener bears against the one or more support members of the second fastener. This arrangement provides an attachment that is secure, but may be readily released.

The respiratory mask assembly may cover a patient's nose only, and may be a so-called nasal mask assembly. The respiratory mask assembly may cover both the nose and mouth of a patient, and may be a so-called full face mask assembly.

The respiratory mask assembly may be adapted to receive a positive pressure from a gas supply whilst maintaining an effective seal with a patient's face. In particular, the mask shell may be movable relative to a patient's face, e.g. towards and away from a patient's face, whilst the sealing cushion deforms to maintain an effective seal with the patient's face. This movement may have a range of at least 3 mm, at least 6 mm, at least 10 mm or at least 15 mm, and hence the membrane may project from the mask shell by at least 3 mm, at least 6 mm, at least 10 mm or at least 15 mm.

According to a third aspect of the present invention, there is provided a respiratory mask assembly comprising a respiratory mask and headgear for retaining the respiratory mask on a patient's face, in use, the headgear including one or more flexible straps and at least one fastener adapted to releasably attach to a corresponding fastener of the respiratory mask, the corresponding fasteners comprise a first fastener having a neck portion and an enlarged head portion, and a second fastener having one or more support members defining an opening for accommodating the neck portion of the first fastener, such that the enlarged head portion of the first fastener bears against the one or more support members of the second fastener.

The first fastener may include abutment surfaces of the enlarged head, which are adapted to abut the one or more support members of the second fastener. The abutment surfaces may have substantially corresponding form to the form of the abutment surfaces of the one or more support members of the second fastener, e.g. substantially mating forms. The abutment surfaces of the first and second fasteners may be curved, for example. The first fastener may be generally T-shaped. The first fastener may be part of the headgear, and may be mounted to a flexible strap of the headgear.

The second fastener may have the form of a hook, which may have at least three limbs, a first limb forming a support member upon which the first fastener bears, and second and third limbs that restrict or prevent transverse movement of the first fastener. The second limb or the third limb may form an attachment to the respiratory mask or the headgear. The second fastener may be generally C-shaped. The second fastener may be part of the respiratory mask, e.g. extending from the mask shell, and may be integrally formed with the mask shell.

The first and second fasteners may be adapted such that relative rotational movement of the fasteners is required in order to disengage the fasteners. This may be achieved by the second fastener having lateral support members with a separation that is less than the lateral width of the enlarged head of the first fastener, in the engaged configuration. This reduces the risk of the fasteners becoming disengagement by accident.

The first and second fasteners may be adapted such that only relative rotational movement of the fasteners is required in order to disengage the fasteners, thereby providing ready disengagement of the fasteners, in use. This may be achieved by at least one of the surfaces of the one or more support members of the second fastener, against which the enlarged head portion of the first fastener bears, being obliquely angled relative to the direction of disengagement, such that relative rotational movement of the fasteners causes the fasteners to be separated in the direction of disengagement. For example, the one or more support members of the second fastener may define a generally V-shaped or concave surface, against which the enlarged head portion of the first fastener bears, when the fasteners are engaged.

One or more surfaces of the first and/or second fastener may be coated with another material, e.g. a material with a higher friction coefficient, such as a thermoplastic elastomer (TPE), in order to improve engagement between the fasteners.

The mask shell may comprise a forehead support formation. The forehead support formation may be integrally formed with the mask shell. The forehead support formation may extend outwardly from the mask shell. The forehead support formation may extend substantially longitudinally outwardly from the mask shell. The forehead support formation may, and most preferably, extend from a corner of the mask shell adapted to be located at the nasal bridge, in use.

The forehead support formation may be adapted to substantially conform to the forehead region of a patient. The forehead support formation may be obliquely angled relative to a longitudinal axis of the mask shell. The forehead support formation may be substantially elongate in form, e.g. substantially elliptical in shape.

The forehead support formation may comprise a forehead rest. The forehead rest may be adapted and/or shaped so as to bear against a forehead of a patient, in use, either directly or through an intermediate component, such as the strap of headgear attached to the forehead support formation. The forehead rest may comprise a patient interface portion. The patient interface portion may comprise a resilient and/or flexible formation. The resilient and/or flexible formation may increase the comfort of a patient.

The forehead support formation may comprise at least one aperture or hook. The at least one aperture or hook may be adapted to releasably receive a headgear strap or the like.

The forehead rest may be moveable relative to the forehead support formation between first and second configurations. The first and second configurations may differ in the thickness of the forehead rest that is presented to the forehead of a patient. Thus, the forehead rest may accommodate patients with a variety of head size.

In an alternative embodiment, the forehead rest is rotatably mounted to the forehead support formation. For example, the forehead support formation may comprise a rotation formation for rotatably receiving a connection formation of the forehead rest. The forehead rest may be rotatable about a longitudinal axis, or a transverse axis.

The forehead rest may be moveable relative to the forehead support formation between first and second configurations. The first and second configurations may differ in the thickness of the forehead rest that is presented to the forehead of a patient. Thus the forehead rest may accommodate patients with a variety of head size.

According to a fourth aspect of the present invention there is provided a respiratory mask assembly, the assembly comprising a mask shell and a sealing cushion, wherein an outer surface of the mask shell has a retaining formation adapted to support a pair of glasses.

The outer surface of the mask shell may be a convex surface of the mask shell. The glasses retaining formation may be upstanding from the outer surface of the mask shell. The glasses retaining formation may be disposed on a nasal bridge region of the mask shell. The glasses retaining formation may comprise a recess for releasably retaining a pair of glasses. The glasses retaining formation may include a fastener, which extends about at least part of the pair of glasses, such that the pair of glasses are retained against the action of gravity.

According to a fifth aspect of the present invention there is provided a respiratory system comprising a respiratory mask assembly as described above.

The respiratory system may comprise a gas supply for supplying gas to the respiratory mask assembly. The gas supply may supply oxygen and/or other breathing gases. The gas supply may supply an anaesthetic, e.g. an anaesthetic gas.

The respiratory system may comprise a ventilator for delivering a supply of breathing gas to the respiratory mask assembly, such that breathing gas may be inhaled by a patient. The ventilator may be a mechanical ventilator. The ventilator may be configured to supply positive pressure ventilation to a patient during at least a portion of a breathing cycle. The ventilator may be configured to supply continuous positive airway pressure, also known as CPAP, to a patient. Thus, the respiratory system may be configured to treat patients suffering from sleep apnoea or the like.

A practicable embodiment of the invention is described in further detail below with reference to the accompanying drawings, of which:

Figure 5:
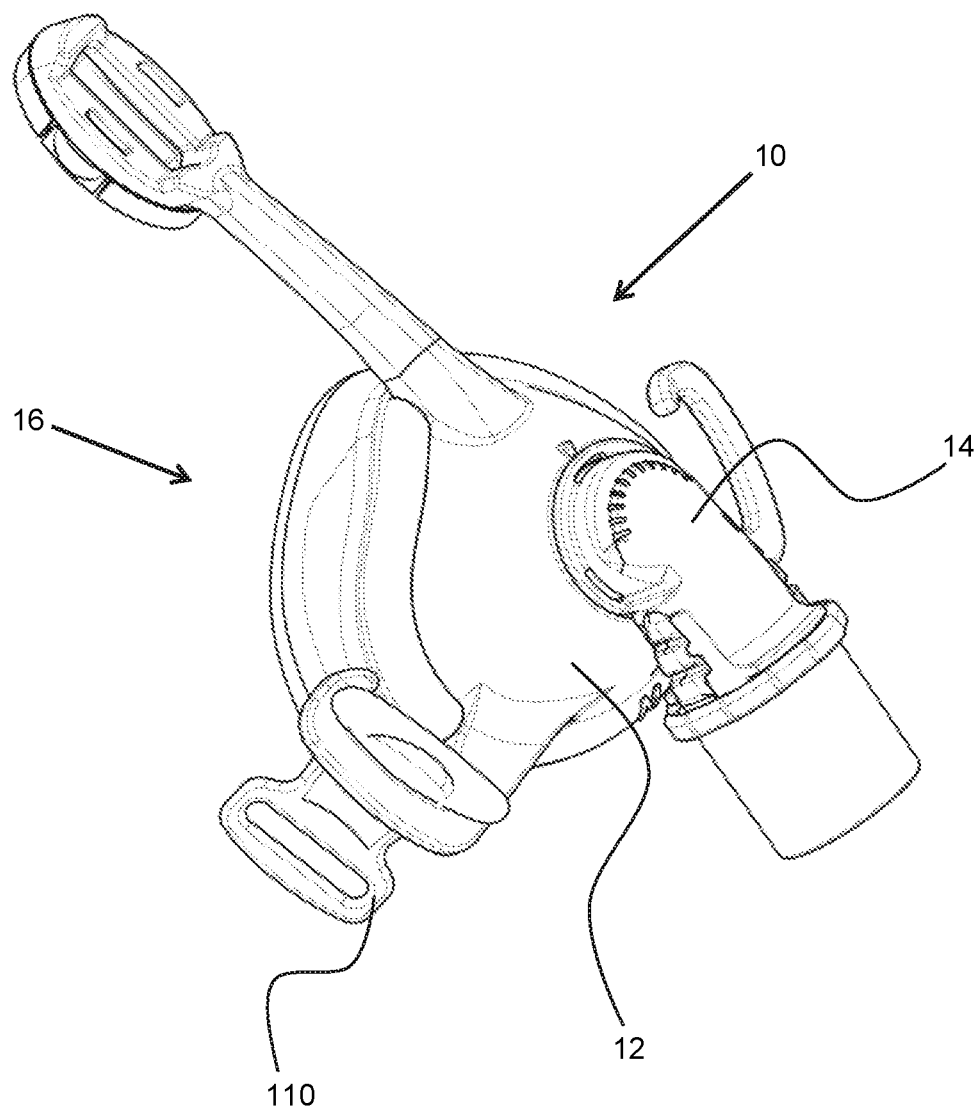
FIG. 5 is a perspective view of an embodiment of a mask assembly according to the second aspect of the present invention.
Figure 6:
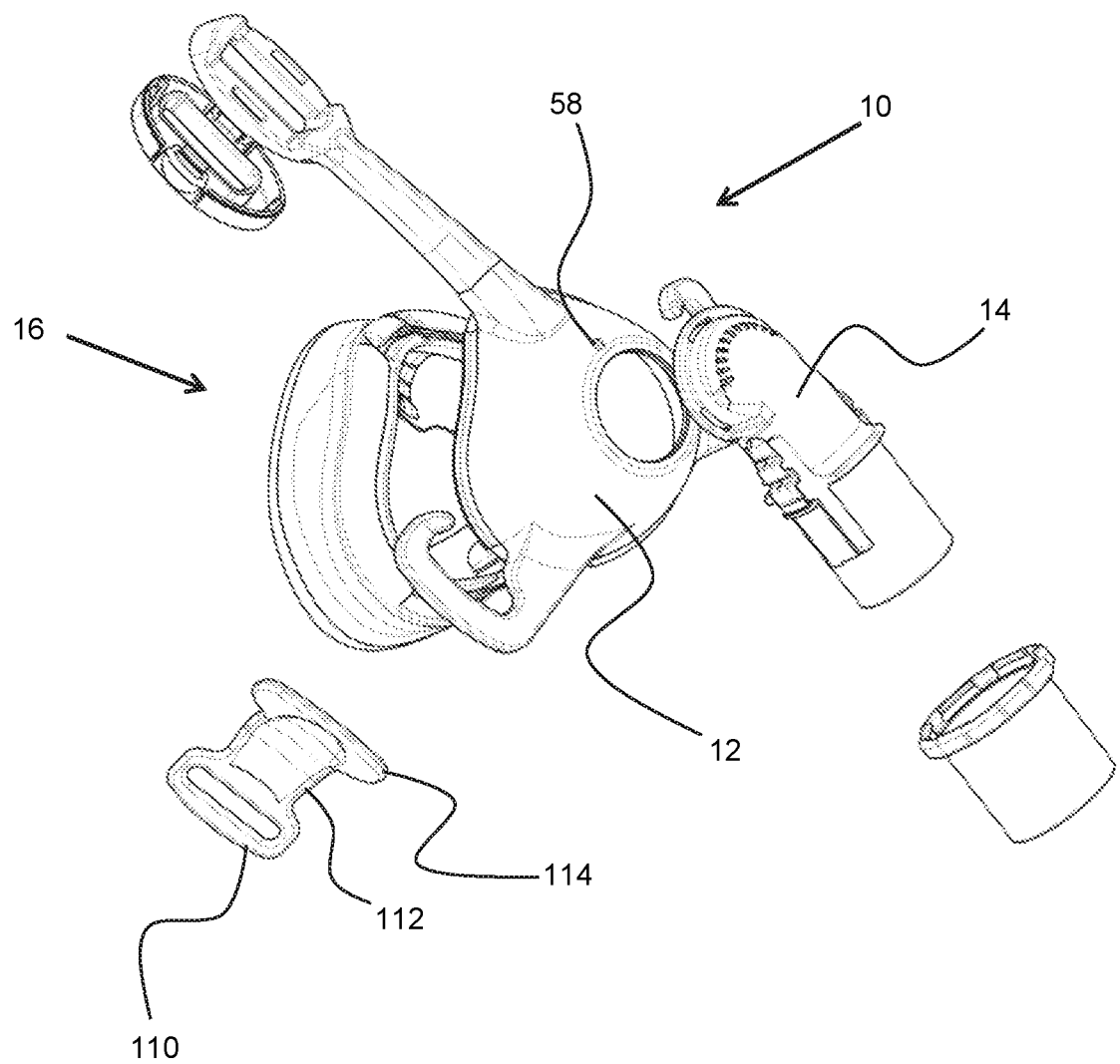
FIG. 6 is an exploded perspective view of the mask assembly of FIG. 5.

A mask assembly according to the present invention, generally designated 10, is shown in FIGS. 5 and 6. The mask assembly 10 comprises a mask shell 12, an elbow connector 14, and a sealing cushion 16.

Figure 1:
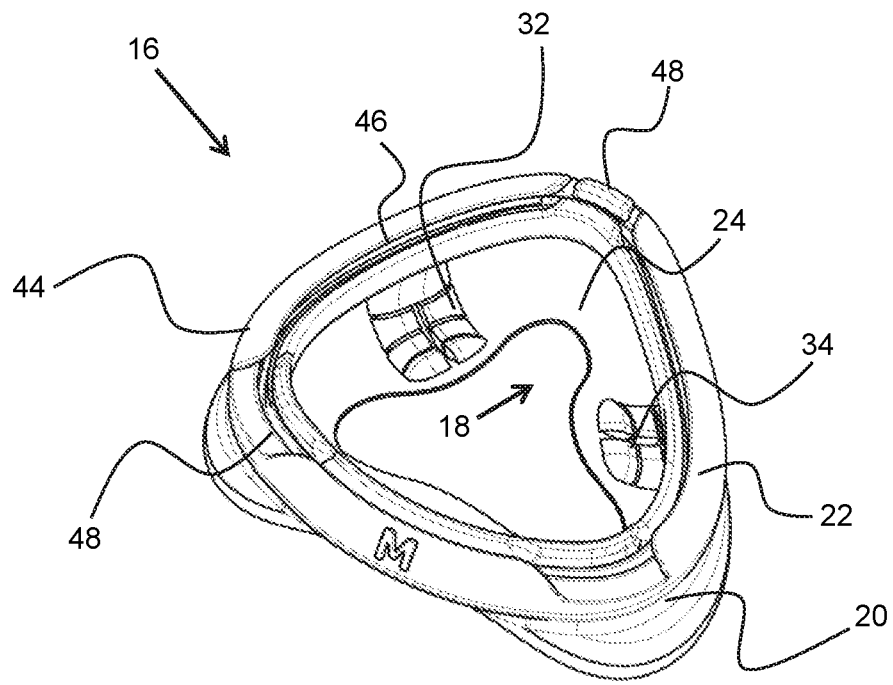
FIG. 1 is a perspective view of an embodiment of a sealing cushion according to the first aspect of the present invention.
Figure 2:
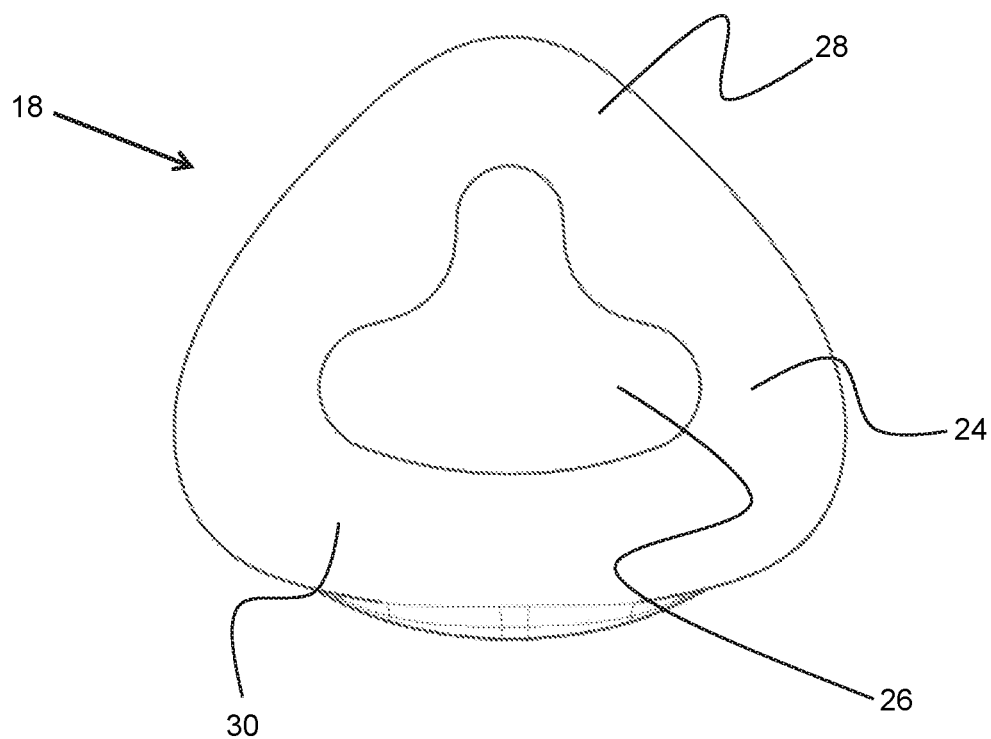
FIG. 2 is a rear view of the sealing cushion of FIG. 1.
Figure 3:
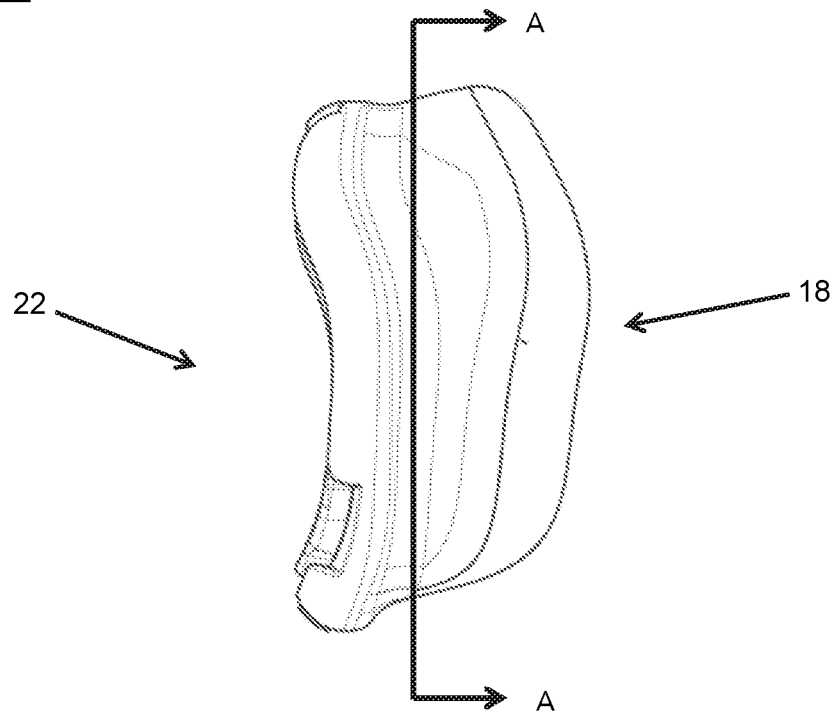
FIG. 3 is a left side view of the sealing cushion of FIG. 1.
Figure 4:
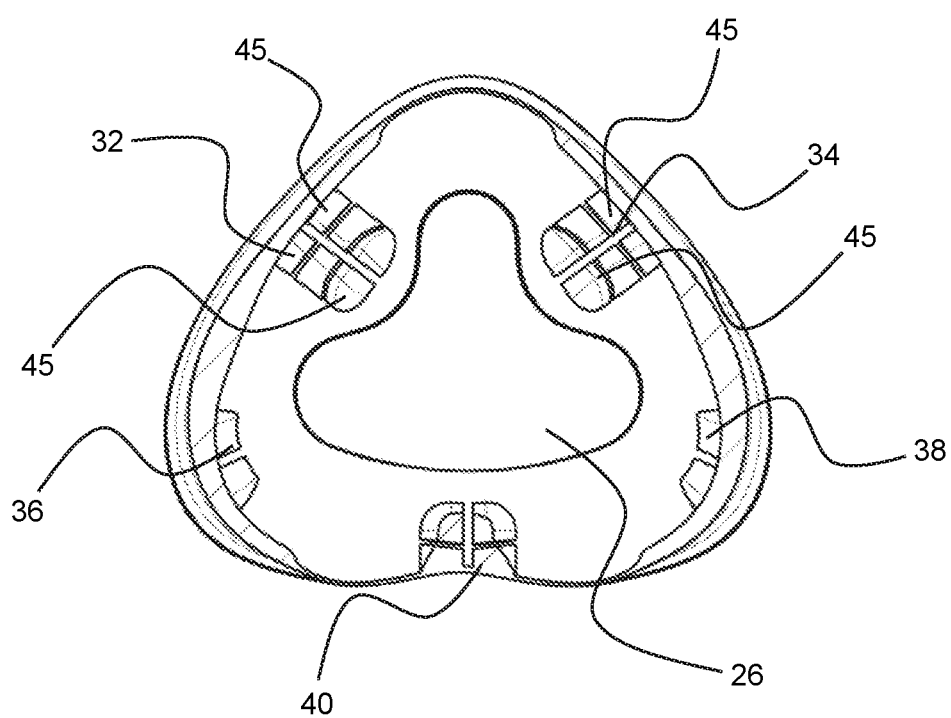
FIG. 4 is a cross-sectional view along the line A-A shown in FIG. 3.

A sealing cushion according to the present invention is shown in FIGS. 1 to 3, which is formed by injection moulding in silicone.

The sealing cushion 16 is substantially triangular in nature, and is shaped so as to substantially surround the nasal region of a patient. Thus, the sealing cushion 16 comprises an aperture 26, which has a shape similar to that of the nasal region of a patient.

The sealing cushion 16 comprises a patient interface portion 18, a side wall portion 20 and a mask shell interface portion 22. The side wall portion 20 extends between, and connects, the patient interface portion 18 and the mask shell interface portion 22, such that an internal cavity is formed within the sealing cushion 16. The patient interface portion 18 comprises a deformable membrane 24. The aperture 26 is provided in the deformable membrane 24.

The membrane 24 is of uniform thickness, which is less than that of the side wall portion 20. The side wall portion 20 is therefore of greater rigidity than the membrane 24, and acts to prevent the membrane 24 from contacting the mask shell interface portion 22 during use. The membrane 24 has a nasal bridge region 28 and a nostril region 30.

The sealing cushion 16 comprises a plurality of support formations 32, 34, 36, 38, 40. Each of the plurality of support formations 32, 34, 36, 38, 40 extends transversely across an internal surface of the membrane 24. Each of the plurality of support formations 32, 34, 36, 38, 40 further extends transversely across an internal surface of the side wall portion 20.

First 32 and second 34 support formations are disposed at either side of the nasal bridge region 28. The first 32 and second 34 support formations extend substantially transversely across the membrane 24 towards the aperture 26. The first support formation 32 is upraised from the interior surfaces of the membrane 24 and side wall 20 and has substantially the form of a trapezoidal prism. The first support formation 32 is formed with a plurality of substantially orthogonal grooves. Thus, the first support formation 32 effectively comprises a plurality of upraised projections 45. Each of the upraised projections 45 has a substantially trapezoidal cross section.

The second support formation 34 has substantially the same form as the first support formation 32.

In a similar manner, third 36 and fourth 38 support formations are disposed at either side of the nostril region 30, such that they are located at lower left and lower right corners of the membrane 24, and a fifth 40 support formation is disposed centrally between the third 36 and fourth 38 support formations, such that it is located at the lower centre of the membrane 24. Each of the third 36, fourth 38, and fifth 40 support formations have the same general form as the first 32 and second 34 support formations. However, the third 36, fourth 38, and fifth 40 support formations extend a shorter distance across the membrane 24 from the side wall 20.

The mask shell interface portion 22 comprises a rim 44 which extends around substantially the entire sealing cushion 16. The rim 44 comprises a groove 46 which extends around substantially all of the perimeter of the mask shell interface portion 22. The groove 46 is dimensioned so as to receive a corresponding projection formed on the mask shell 12. The groove has portions of enlarged depth located along each major axis of the mask shell interface portion 22, but not at the corners of the mask shell interface portion 22, such that the corresponding projections formed on the mask shell 12 may be received with a snap fit.

Figure 7:
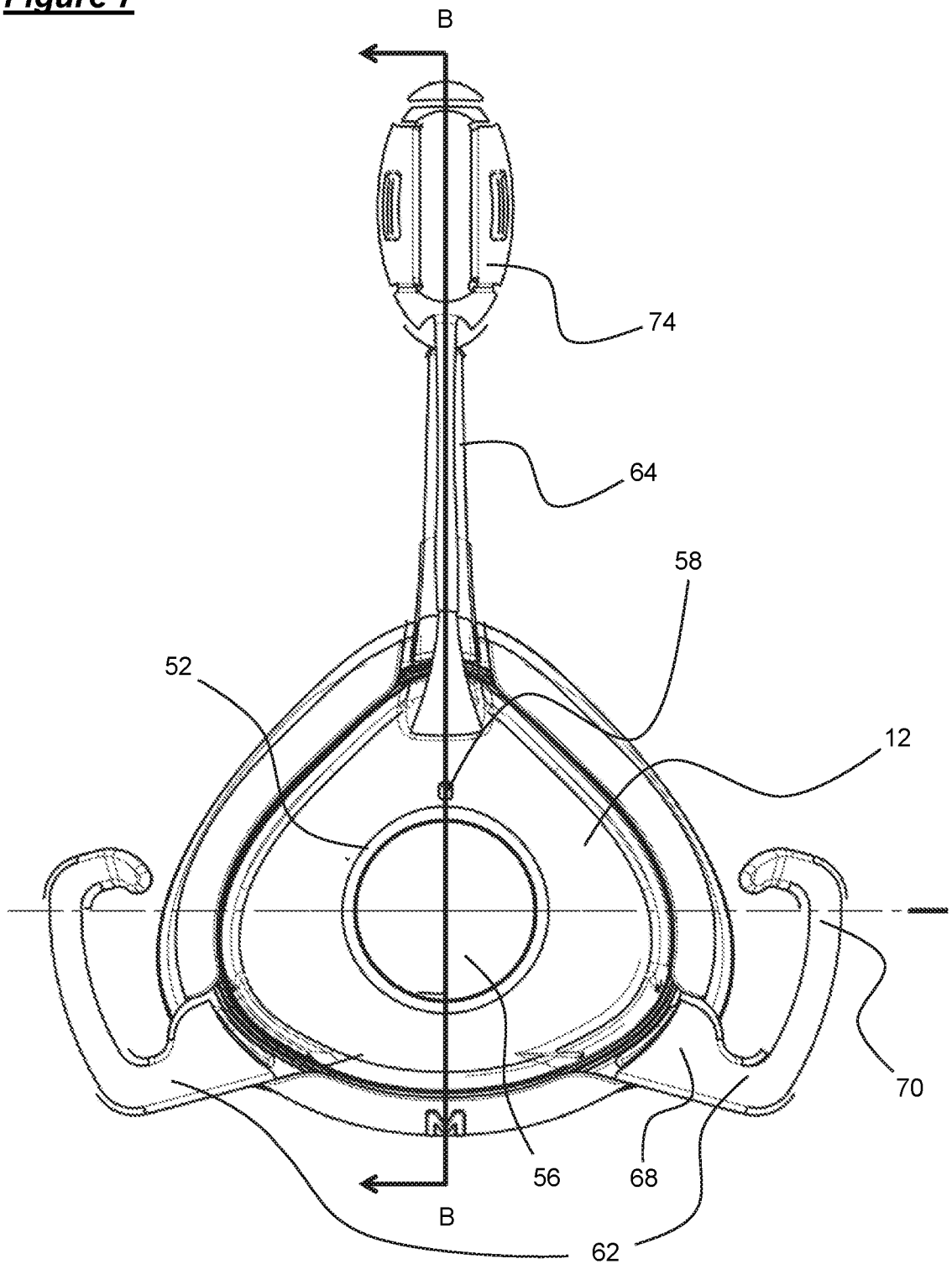
FIG. 7 is a front view of the mask assembly of FIG. 5.
Figure 8:
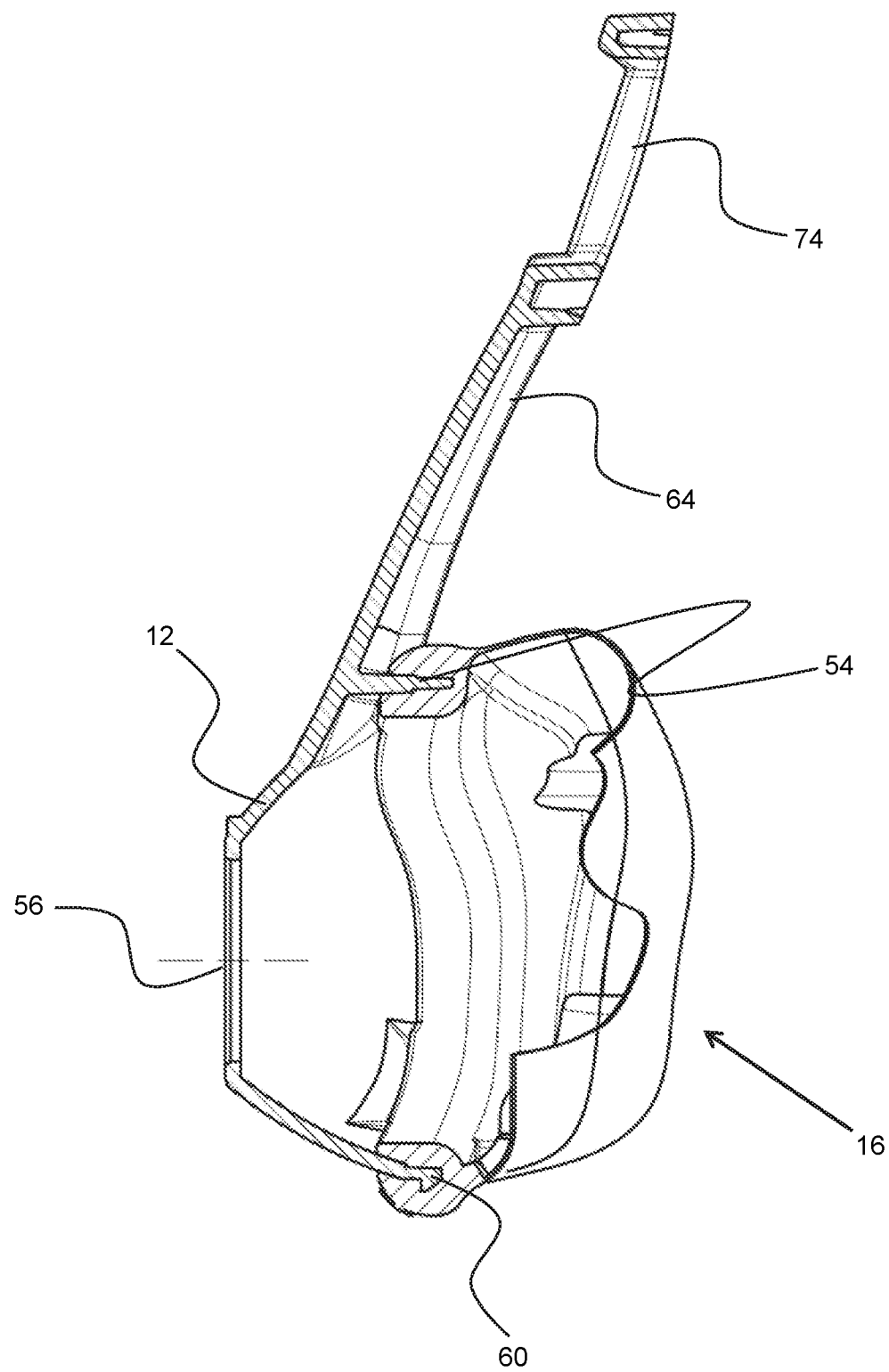
FIG. 8 is a cross-section along the line B-B shown in FIG. 7.

A mask shell 12 according to the present invention is shown more clearly in FIGS. 6, 7, and 8.

The mask shell 12 is substantially triangular in nature, and is shaped so as to correspond to the mask shell interface portion 22 of the sealing cushion 16. The mask shell 12 is generally dome-shaped, such that the mask shell 12 has an internal cavity.

A mask shell aperture 56 is located at the apex of the dome-shaped mask shell 12, and is substantially circular in nature. A frontal ridge 52 is upstanding from an exterior surface of the mask shell 12, and is disposed circumferentially about the mask shell aperture 56. The frontal ridge 52 has a substantially rectangular cross-section.

A rearward ridge 54 extends rearwardly from the peripheral edge of the mask shell 12. The rearward ridge 54 extends into the mask shell interface portion 22 of the sealing cushion 16 when assembled. The rearward ridge 54 has a substantially rectangular cross section, and has a width which is substantially the same as that of the groove 46 that is present on the mask shell interface portion 22 of the sealing cushion 16.

A plurality of clip projections 60 are integrally formed with the rearward ridge 54, and are located along each edge of the mask shell 12, but are not present at the corners. The plurality of clip projections 60 each have a substantially rectangular cross section, and each of the plurality of clip projections 60 have a width which is greater than the width of the rearward ridge 54. Each of the plurality of clip projections 60 is dimensioned so as to be received within a corresponding portion of enlarged depth of the groove disposed on the mask shell interface portion 22 of the sealing cushion 16.

A retaining formation 58 comprises an upstanding projection, and is disposed centrally on the upper circumference of the first frontal ridge 52. This retaining formation 58 is adapted to engage a corresponding recess in the elbow connector 14, when the elbow connector 14 is orientated with its distal end directed towards the top of the patient's head. This may enable a patient to maintain a connected respiratory tube over the top of their head, if they find this a more comfortable position to sleep.

A pair of strap retaining formations 62 are located at lower left and right corners of the mask shell 12. The pair of strap retaining formations 62 each extend laterally outwardly from the body of the mask shell 12. The plurality of strap retaining formations 62 are integral with the mask shell 12, and are formed as part of the same injection moulding process that is used to form the mask shell 12.

Each of the of strap retaining formations 62 comprise first 68 and second 70 arm-like portions. The first arm-like portion 68 extends laterally outwardly from the mask shell 12, and the second arm like portion 70 extends substantially orthogonally from the first arm-like portion 68 in the same vertical plane. The second arm-like portion 70 is curved in nature, such that a distal end of the second arm-like portion 70 extends substantially towards the mask shell 12. Thus, each of the of strap retaining formations 62 are hook-like in form.

A forehead support formation 64 is located at the uppermost corner of the triangularly shaped mask shell 12. The forehead support formation 64 is elongate, and extends vertically outwardly from the mask shell 12. The forehead support formation 64 is integral with the mask shell 12 and is formed as part of the same injection moulding process as that which forms the mask shell 12.

The forehead support formation 64 is obliquely angled relative to the mask shell 12, so as to conform to the plane of a patient's forehead. The forehead support formation 64 has a substantially rectangular cross section. The cross section of the forehead support formation 64 is not constant along its length, and the forehead support formation 64 is tapered towards a distal end.

Figure 9:
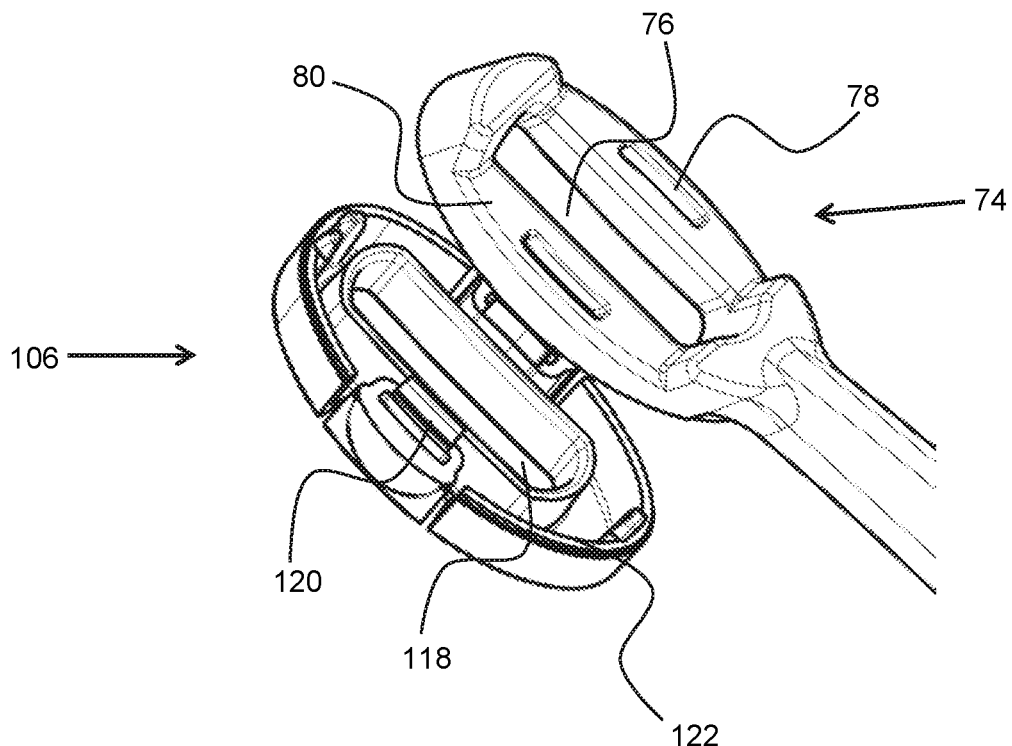
FIG. 9 is an enlarged perspective view of a forehead rest which forms part of the mask assembly of FIG. 5.

A close-up view of the distal end of the forehead support formation 64 is shown in FIG. 9. The distal end of the forehead support formation 64 comprises a forehead rest 74. The forehead rest 74 is integral with the forehead support formation 64, and is formed as part of the same injection moulding process. The forehead rest 74 is substantially elliptical in form, and is positioned such that its semi-major axis lies in a substantially vertical direction.

The forehead rest 74 comprises a central slot 76 and a plurality of apertures 78. The central slot 76 is substantially rectangular in form, and extends across substantially all of the semi-major axis of the forehead rest 74. Thus, the forehead rest 74 has a hollow central portion in the form of central slot 76, and a rim 80.

The plurality of apertures 78 are located on the rim 80, and are substantially rectangular in form. The width of the central slot 76 is greater than twice the width of each of the plurality of apertures 78. Each of the plurality of apertures 78 are disposed centrally around the rim 80.

A removable forehead spacer 106 is substantially elliptical in form, and is positioned such that its semi-major axis lies in a substantially vertical direction.

The forehead spacer 106 comprises a central slot 118 and a plurality of spigots 120. The central slot 118 is substantially rectangular in form, and extends across substantially all of the semi-major axis of the forehead spacer 106. Thus, the forehead spacer 106 has a hollow central portion in the form of central slot 118, and a rim 122.

The plurality of spigots 120 are located on the rim 122, and are substantially rectangular in form. The width of the central slot 118 is greater than twice the width of each of the plurality of spigots 120. Each of the plurality of spigots 120 are disposed centrally around the rim 122. The plurality of spigots 120 are shaped so as to be inserted into the plurality of apertures 78 disposed on the forehead rest 74 with a snap fit.

The forehead spacer 106 is removable from engagement with the forehead rest 74, and thus provides a way of accommodating a wide variety of patients that have different sized foreheads. In particular, the mask may be used with or without the forehead spacer 106, depending on the preference of the patient. The forehead spacer 106 is keyed so that it can only be assembled in the correct orientation.

Figure 12:
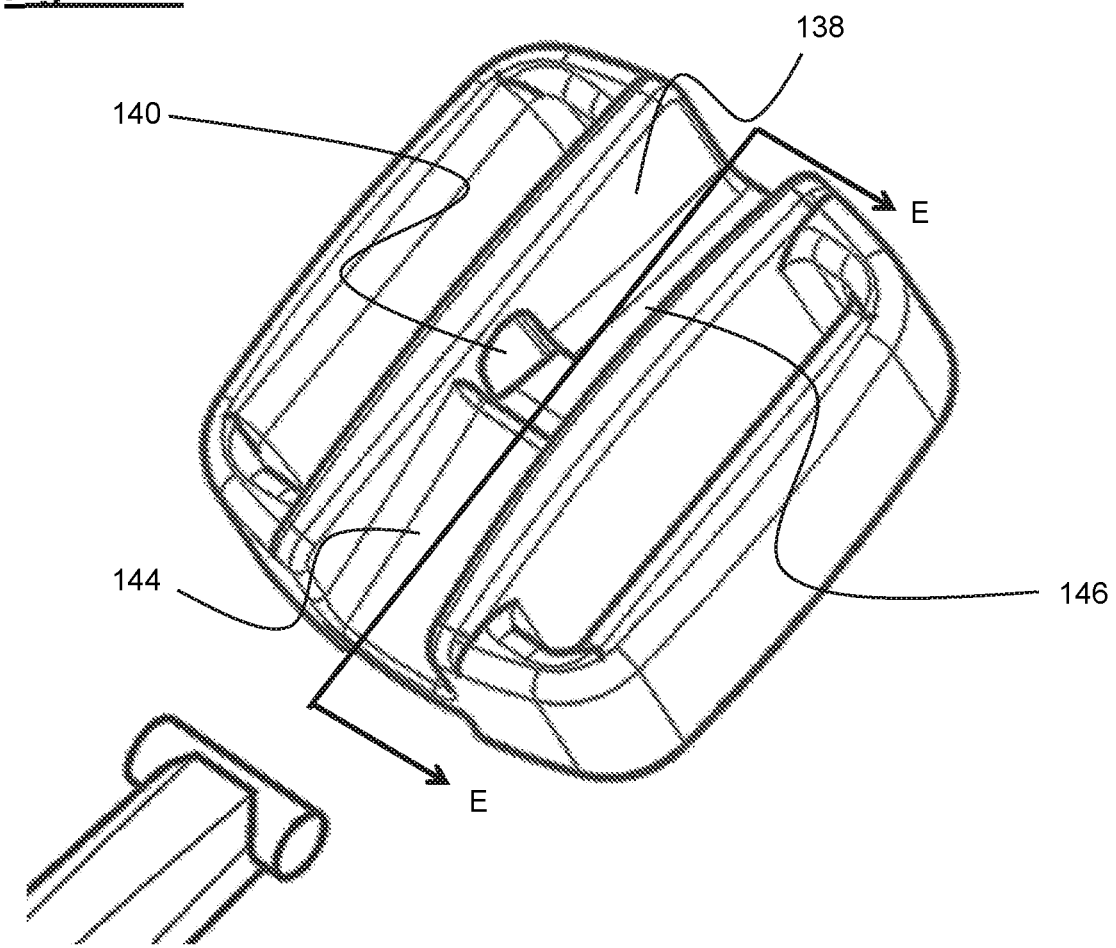
FIG. 12 is an exploded perspective view of an alternative forehead rest for the mask assembly of FIG. 5 in a first configuration
Figure 13:
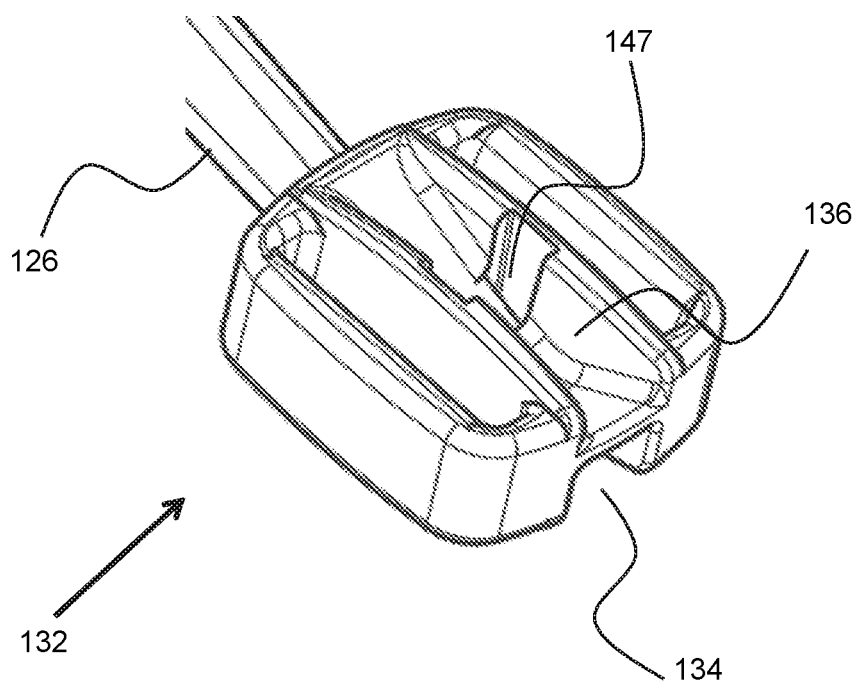
FIG. 13 is a perspective view of an alternative forehead rest for the mask assembly of FIG. 5 in a second configuration.
Figure 14:
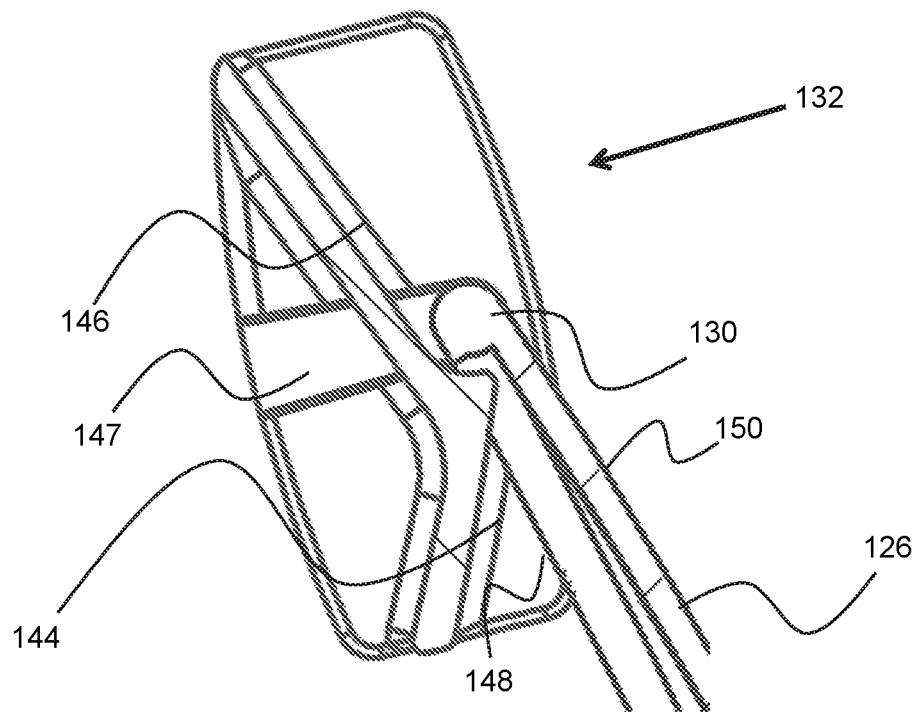
FIG. 14 is a cross-section through the line E-E shown in FIG. 12 when the forehead rest is assembled.

An alternative forehead support formation 126 and forehead rest 132 are shown in FIGS. 12, 13 and 14.

A distal end of the forehead support formation 126 comprises a bar 130, and a forehead rest 132. The bar 130 is substantially cylindrical in form, and is orthogonal to the forehead support formation 126. The bar 130 is wider than the distal end of the forehead support formation 126, such that the ends of the bar 130 project orthogonally outwardly from the distal end of the forehead support formation 126.

The forehead rest 132 is substantially cuboidal in form. The forehead rest 132 comprises first 134 and second 136 channels located on opposing sides the forehead rest 132. Both the first 134 and second 136 channels extend across substantially all of the length of the forehead rest. Both of the first 134 and second 136 channels have a width that is approximately one third of the width of the forehead rest 132. Both the first 134 and the second 136 channels are located centrally on the forehead rest 132. The first 134 and second 136 channels have different depths, and the first channel 134 is deeper than the second channel 136.

The first channel 134 comprises a plurality of sidewalls 138. Each sidewall 138 comprises a recess 140. The recesses 140 are substantially cylindrical in form. The recesses 140 are located centrally along the first channel 134. The diameter of each recess 140 is substantially the same as that of the diameter of the bar 130. Thus, the bar 130 may be located within the plurality of recesses 140, such that the forehead rest 132 is held in place. The forehead rest 132 is thereby rotatable around the bar 130.

The first channel 134 further comprises a base wall. The base wall comprises first 144 and second 146 portions. The first portion 144 extends across slightly less than half of the length of the first channel 134. The second portion 146 extends across the remainder of the length of the first channel 134.

The first portion 144 is tapered, such that the depth of the first channel 134 is greater at a first peripheral edge of the forehead rest 132 than it is at the central region of the first channel 134. The second portion is tapered, such that the depth of the first channel 134 is greater at an opposing peripheral edge of the forehead rest 132 than it is at the central region of the first channel 134. The angle of the taper of the first portion 144 is greater than the angle of the taper of the second portion 146. The base wall thus has the form of a scalene triangle.

The second channel 136 comprises a plurality of sidewalls. Each sidewall 144 comprises a recess 147. The recesses 147 are substantially rectangular in form, and extend across substantially all of the depth of the second channel 136.

When the forehead rest 132 is initially located upon the bar 130, the first portion 144 of the base wall is located such that it is in engagement with a rear surface 148 of the forehead support formation 126. This is the first configuration. The forehead rest 130 may be rotated around the bar 130, such that the second portion 146 of the base wall is in engagement with a front surface 150 of the forehead support formation. This is the second configuration.

The taper of the first 144 and second 146 portions of the base wall is such that the forehead rest 132 extends rearwardly by a greater distance when it is in the first configuration than when the forehead rest 132 is in the second configuration. Thus, the forehead rest is adjustable in order to accommodate patients having a wide variety of forehead sizes.

Figure 10:
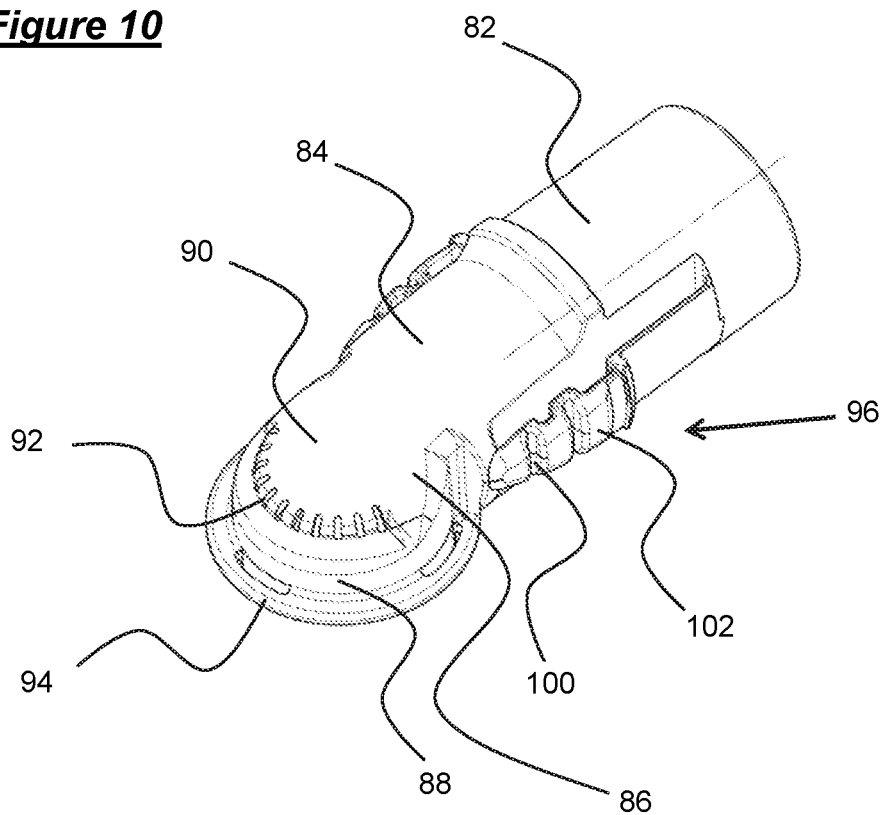
FIG. 10 is a perspective view of an elbow connector which forms part of the mask assembly of FIG. 5.
Figure 11:
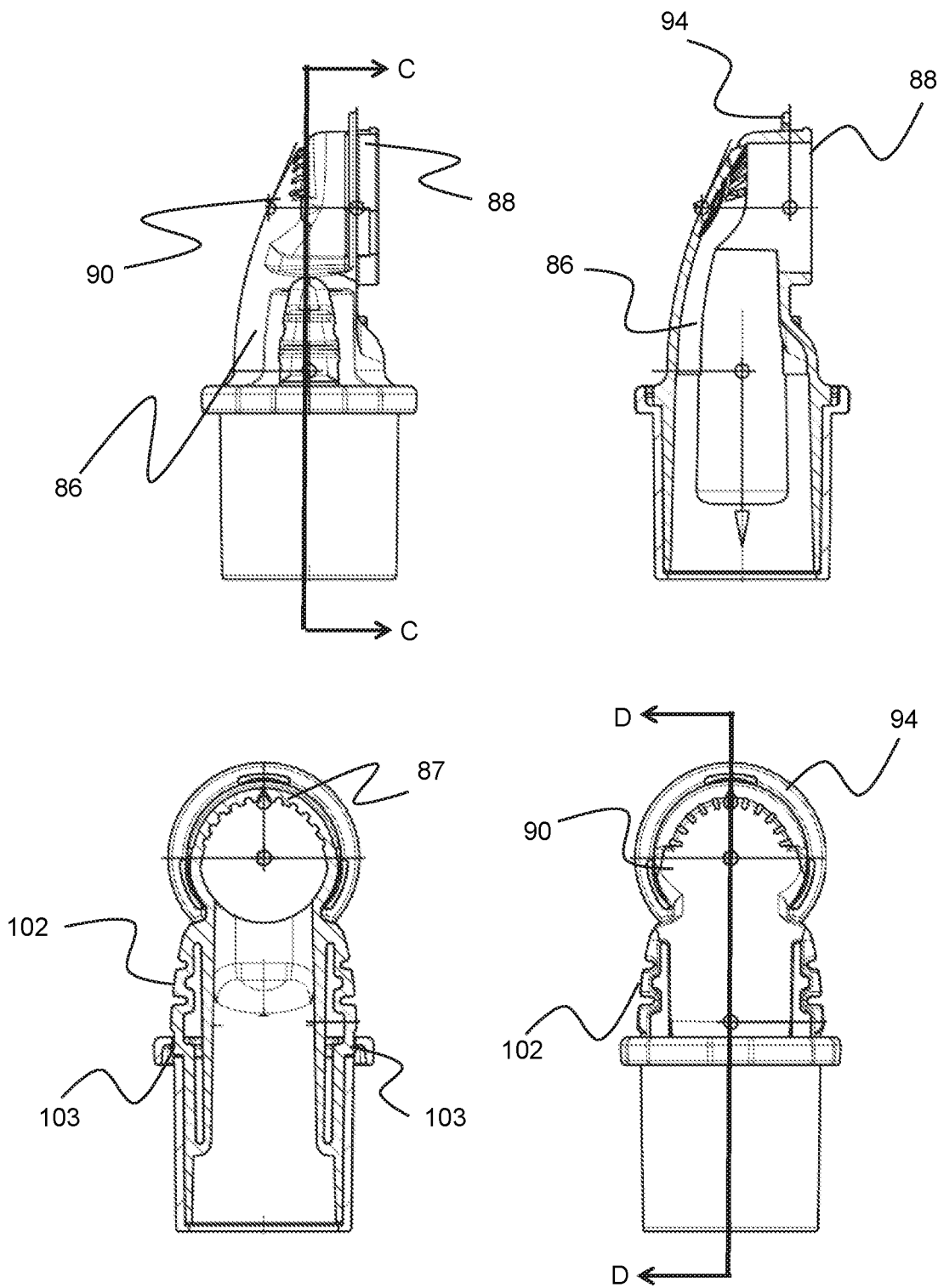
FIG. 11 shows, counter-clockwise from top left: a left view of an elbow connector which forms part of the mask assembly of FIG. 5; a cross-section along the line C-C, a front view of an elbow connector which forms part of the mask assembly of FIG. 5; and a cross-section along the line D-D.

An elbow connector 14 according to the present invention is shown in FIGS. 10 and 11.

The elbow connector 14 comprises a lower portion 82 and an upper portion 84. The lower portion 82 is substantially cylindrical in form. Both the lower 82 and upper 84 portions are hollow. The upper portion 84 comprises first 86 and second 88 perpendicular limbs. The second limb 88 is of a significantly shorter length than the first limb 86, such that the upper portion 84 of the elbow connector 14 resembles a severely truncated "L-shape" or elbow.

The first limb 86 interfaces with the second limb 88 at a region that is disposed along a substantially central axis of the first limb 86. Thus, approximately a radius of the first limb 86 extends rearwardly underneath the second limb 88. The elbow connector 14 may thereby protrude outwardly from a mask shell 12 by a distance that is significantly less than those elbow connectors known in the prior art. A frontal surface 90 of the first limb 86 is tapered, such that the frontal surface 90 curves towards the interface region. The tapered nature of the first limb 86 gives the interface between the first 86 and second 88 limbs a substantially circular appearance.

The first limb 86 comprises a plurality of apertures 92. The apertures 92 are located on the frontal surface 90, and are substantially rectangular in form. The apertures 92 are disposed in a series, in a semi-circular arrangement around the interface between the first 86 and second 88 limbs. The apertures 92 are thereby in fluid communication with both the first 86 and second limbs 88, and function as exhalation vents for the elbow connector 14.

The first limb 86 comprises a resiliently deformable rim 87, which engages the corresponding frontal ridge 52 of the mask shell 12.

The second limb 88 is substantially cylindrical in form. The second limb 88 comprises a peripheral upstanding rim 94. The peripheral upstanding rim 94 extends around substantially the entirety of the circumference of the second limb 88. The diameter of the second limb 88 is substantially the same as the diameter of the aperture 56 of the mask shell 12.

The elbow connector 14 further comprises a plurality of quick release clips 96. The quick release clips 96 are elongate in form, and are disposed upon opposing sides of the elbow connector 14. The clips 96 extend between the lower portion 82 of the elbow connector 14, and the first limb 86 of the upper portion 84 of the elbow connector. Opposing ends of the quick release clips 96 are attached to the elbow connector 14, such that substantially all of the body of the quick release clips 96 is upstanding from the elbow connector 14.

Each of the plurality of quick release clips 96 comprises a connecting formation 103. The connecting formation 103 takes the form of a circumferentially extending protrusion disposed in a lower region of the quick release clip 96. The connecting formation 103 is shaped to releasably retain a respiratory tube connector and/or any other such appropriate respiratory circuit component. An end portion of a respiratory tube can be advanced over the plurality of quick release clips 96, until a corresponding recess of the end portion engages the connecting formation 103.

The quick release clip 96 comprises a series of channels 100 and ridges 102, such that the quick release grip comprises a grip formation. Each grip formation is formed of a resiliently deformable material. Thus, each grip formation may be depressed upon application of pressure by a user.

In order to release the respiratory tube, the grip formations are depressed, thereby depressing the resiliently deformable connecting formation 103 at the same time, and the respiratory tube may be simply pulled away.

The mask assembly 10 further comprises headgear, not shown in the Figures, for fastening the mask assembly 10 to the head of a patient. The headgear includes a plurality of straps which are engageable with the forehead rest 74 and strap retaining formations 62 of the mask shell.

The headgear comprises a plurality of retaining formations 110 for engaging the corresponding strap retaining formations 62 of the mask shell 12.

The retaining formations 110 comprise a substantially rectangular main body 112, and end toggles 114, of which only one end toggle 114 is shown in the Figures. The width of the toggles 114 is greater than the width of the main body 112, such that the shape of the retaining formations 110 resembles that of a bow. An end toggle 114 is provided with an aperture, which receives a loop of a headgear strap. The end toggle 114 is shaped so as to correspond with, and be retained by the plurality of strap retaining formations 62 of the mask shell 12.

Such a toggle-like arrangement allows the headgear strap to be securely retained, whilst also allowing for quick and easy removal.

Similarly, a loop of a strap, or two straps, of the headgear may be received within the central slot 76 of the forehead rest 74, so as to retain the mask assembly in place relative to the face of a patient.

To assemble the parts of the mask assembly 10, the groove 46 and clip receiving formations 48 of the sealing cushion 16 are aligned with the ridge 54 and clip projections 60 of the mask shell 12. The ridge 54 and clip projections 60 are received within the groove 46 and clip receiving formations 48, respectively, with a snap fit.

The second limb 88 of the elbow connector 14 is received within the aperture 56 of the mask shell 12 with a snap fit. The elbow connector 14 is rotatable around an axis that is orthogonal to the plane of the aperture 56 of the mask shell.

When in use, the sealing cushion 16 is located over the nasal region of a patient. The toggles 114 are received within the strap receiving formations 62, and the headgear assembly is positioned at the rear of a patient's head, such that the strap acts so as to retain the mask assembly 10 in a desired position. Thus, the mask assembly 10 urges the sealing cushion 16 against the face of a patient, ensuring that an airtight seal is formed.

The forehead spacer 106 may optionally be connected to the forehead rest 74.

A respiratory tube 124 is connected to the elbow connector 14, such that a lip 126 of the respiratory tube 124 is retained by a channel 100 of the connecting formation of the quick release clips 96.

The respiratory tube 124 allows a flow of oxygen or pressurised gases to be provided to the mask assembly 10, which may then be inhaled by the patient.

Figure 15:
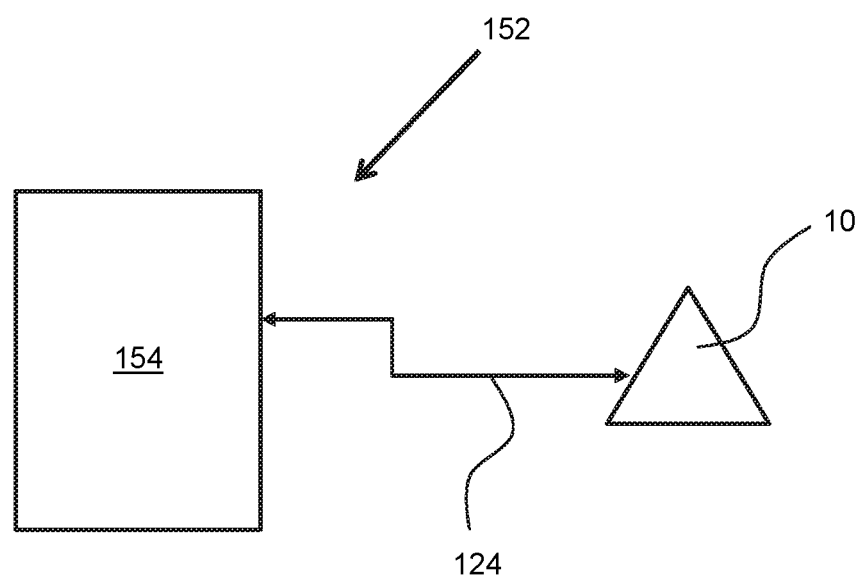
FIG. 15 is a schematic view of a respiratory system comprising a respiratory mask of the present invention.

Referring now to FIG. 15, a respiratory system 152 comprising respiratory mask assembly 10 is shown schematically. The respiratory system 152 may comprise a ventilator 154 for delivering a supply of breathing gas to the respiratory mask assembly 10 through respiratory tube 124, such that breathing gas may be inhaled by a patient. The ventilator 154 may be a mechanical ventilator. The ventilator may be configured to supply positive pressure ventilation to a patient during at least a portion of a breathing cycle. The ventilator 154 may be configured to supply continuous positive airway pressure, also known as CPAP, to a patient. Thus, the respiratory system 152 may be configured to treat patients suffering from sleep apnea or the like.

The invention claimed is:

1. A sealing cushion for a respiratory mask assembly, the sealing cushion comprising: a patient interface portion having a resiliently deformable membrane for contact with a patient's face, and an aperture formed therein for receiving a nasal and/or mouth region of the patient's face, wherein an inner surface of the deformable membrane comprises a plurality of projections extending therefrom, the plurality of projections arranged in separate support formations positioned in three or more discrete regions on the inner surface of the deformable membrane, the projections in each of the separate support formations being arranged such that each projection in one support formation directly engages with an adjacent projection in the one support formation when the deformable membrane is deformed as a result of contact of the deformable membrane with the patient's face, in use, thereby providing the deformable membrane with an increased resistance to further deformation, wherein each of the separate support formations extend in a traverse direction across the deformable membrane, at least one of the separate support formations having at least two orthogonal grooves or channels between adjacent projections in the at least one of the separate support formation, wherein each of the separate support formations are separated from each other by a spacing that defines a region on the inner surface of the deformable membrane that does not comprise said plurality of projections.

2. The sealing cushion as claimed in claim 1, wherein a height of each projection of the plurality of projections is at least double a thickness of the deformable membrane.

3. The sealing cushion as claimed in claim 1, wherein a width and/or length of each projection of the plurality of projections is at least double a thickness of the deformable membrane.

4. The sealing cushion as claimed in claim 1, wherein two or more of the separate support formations are shaped, sized, or arranged to provide different levels of resilience and/or resistance to deformation.

5. The sealing cushion as claimed in claim 1, wherein one or more of the separate support formations are located in a nasal bridge region of the deformable membrane and comprise larger projections than one or more of the separate support formations located in corners of the deformable membrane located opposite the nasal bridge region.

6. The sealing cushion as claimed in claim 1, wherein the projections in each of the separate support formations extend in a traverse direction across substantially the entire deformable membrane.

7. The sealing cushion as claimed in claim 1, wherein the separate support formations are located either (i) on both sides of a nasal bridge region of the deformable membrane, (ii) in corners of the deformable membrane opposite the nasal bridge region, or (iii) both (i) and (ii).

8. The sealing cushion as claimed in claim 1, wherein a series of three or more adjacent projections in one or more of the support formations are adapted to be brought into direct engagement simultaneously, as the deformation of the deformable membrane increases.

9. The sealing cushion as claimed in claim 1, wherein a series of three or more adjacent projections in one or more of the support formations are adapted to be brought into direct engagement sequentially, as the deformation of the deformable membrane increases.

10. The sealing cushion as claimed in claim 1, wherein at least two projections of the plurality of projections in a first region of the deformable membrane are adapted to engage one another before engagement of at least two projections in a second region of the deformable membrane during engagement of the deformable membrane with the patient's face, in use.

11. The sealing cushion as claimed in claim 1, wherein one or more of the plurality of projections are tapered in a transverse direction, such that the one or more tapered projections reduce in width and/or height towards an inner edge of the deformable membrane that defines the aperture.

12. The sealing cushion as claimed in claim 1, wherein one or more of the plurality of projections are tapered in a circumferential direction, such that the one or more tapered projections of the plurality of tapered projections provide a graduated transition between regions of greater and regions of lesser resilience and/or resistance to deformation.

13. The sealing cushion as claimed in claim 1, wherein one or more of the plurality of projections is separated from an adjacent projection in the same support formation as the one or more of the plurality of projections by a V-shaped channel or groove.

14. The sealing cushion as claimed in claim 1, wherein the deformable membrane is curved in cross-section in a region of the deformable membrane that is deformed during use, and where the curvature increases when the deformable membrane is deformed by engagement with patient's face, the engagement between each of the projection in the one support formation with the adjacent projection in the one support formation being caused by the increase in curvature of the deformable membrane.

15. The sealing cushion as claimed in claim 1, wherein the deformable membrane comprises a single membrane.

16. The sealing cushion as claimed in claim 1, wherein the plurality of projections are integrally formed with the deformable membrane.

17. The sealing cushion as claimed in claim 1, wherein the plurality of projections arranged in the separate support formations positioned in the three or more discrete regions of the deformable membrane comprise first and second support formations positioned in a nasal bridge region of the deformable membrane, and one or more additional support formations positioned in (i) corners of the deformable membrane located opposite the nasal bridge region, (ii) below the nasal bridge region and centrally between corners of the deformable membrane, or (iii) both (i) and (ii).

18. The sealing cushion as claimed in claim 1, wherein each of the separate support formations have at least two orthogonal grooves or channels between adjacent projections in each of the respective separate support formations.

19. A respiratory mask assembly comprising a sealing cushion as claimed in claim 1.

20. A respiratory system comprising a respiratory mask assembly as claimed in claim 19.

21. The respiratory system as claimed in claim 20, wherein the respiratory system comprises a ventilator for delivering a supply of breathing gas to the respiratory mask assembly, and the ventilator is configured to supply positive pressure ventilation to a patient during at least a portion of a breathing cycle.

22. A sealing cushion for a respiratory mask assembly, the sealing cushion comprising: a patient interface portion having a resiliently deformable membrane for contact with a patient's face, and an aperture formed therein for receiving a nasal and/or mouth region of the patient's face, wherein an inner surface of the deformable membrane comprises a plurality of projections extending therefrom, the plurality of projections arranged in separate support formations positioned in a plurality of localized regions on the inner surface of the deformable membrane, the projections in each of the separate support formations being arranged such that each projection in one support formation directly engages with an adjacent projection in the one support formation when the deformable membrane is deformed as a result of contact of the deformable membrane with the patient's face, in use, thereby providing the deformable membrane with an increased resistance to further deformation, wherein each of the separate support formations extend in a traverse direction across the deformable membrane, at least one of the separate support formations having at least two orthogonal grooves or channels between adjacent projections in the at least one of the separate support formation, wherein each of the separate support formations are separated from each other by a spacing that defines a region on the inner surface of the deformable membrane that does not comprise said plurality of projections.

23. The sealing cushion as claimed in claim 22, wherein each of the separate support formations have at least two orthogonal grooves or channels between adjacent projections in each of the respective separate support formations.

\* \* \* \* \*